(12) United States Patent
Pratt et al.

(10) Patent No.: US 10,932,954 B2
(45) Date of Patent: Mar. 2, 2021

(54) CUSTOMIZABLE CLOSED TISSUE SITE DRESSING FOR IMPROVED POSTOPERATIVE REMOVAL

(71) Applicant: KCI Licensing, Inc., San Antonio, TX (US)

(72) Inventors: Benjamin Andrew Pratt, Poole (GB); Colin John Hall, Poole (GB)

(*) Notice: Subject to any disclaimer, the term of this patent is extended or adjusted under 35 U.S.C. 154(b) by 585 days.

(21) Appl. No.: 15/546,268

(22) PCT Filed: Jan. 23, 2016

(86) PCT No.: PCT/US2016/014645
§ 371 (c)(1),
(2) Date: Jul. 25, 2017

(87) PCT Pub. No.: WO2016/126444
PCT Pub. Date: Aug. 11, 2016

(65) Prior Publication Data
US 2018/0333522 A1    Nov. 22, 2018

Related U.S. Application Data

(60) Provisional application No. 62/110,870, filed on Feb. 2, 2015.

(51) Int. Cl.
*A61F 13/00* (2006.01)
*A61M 1/00* (2006.01)
*A61F 13/14* (2006.01)

(52) U.S. Cl.
CPC ...... *A61F 13/00068* (2013.01); *A61F 13/148* (2013.01); *A61M 1/0031* (2013.01);
(Continued)

(58) Field of Classification Search
CPC ... A61M 1/008; A61M 1/0088; A61M 1/0086
See application file for complete search history.

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 82 | 3/1986 |
| AU | 745271 B2 | 3/2002 |

(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery.

(Continued)

*Primary Examiner* — Susan S Su

(57) ABSTRACT

Some illustrative embodiments of a dressing for treating a tissue site may include a fluid hub, a plurality of elongate fluid members, and a separable joint. The plurality of elongate fluid members may be positioned in fluid communication with the fluid hub. Each of the plurality of elongate fluid members may include a proximal end, a distal end, and an elongate side between the proximal end and the distal end. The elongate side of the elongate fluid members may extend longitudinally outward from the fluid hub. The separable joint may be coupled between the elongate side of one of the plurality of elongate fluid members and the elongate side of another of the plurality of elongate fluid members. Other dressings, systems, and methods are disclosed.

33 Claims, 7 Drawing Sheets

(52) U.S. Cl.
CPC ........ *A61M 1/0086* (2014.02); *A61M 1/0088* (2013.01); *A61M 2210/1021* (2013.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,692,153 A * | 9/1987 | Berlin ................ A61M 27/00 604/171 |
| 4,710,165 A | 12/1987 | McNeil et al. |
| 4,717,379 A * | 1/1988 | Ekholmer ........... A61M 25/007 604/43 |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,925,452 A * | 5/1990 | Melinyshyn .......... A61M 25/00 138/111 |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,395 A * | 3/1992 | Rosenberg .......... A61M 1/0005 604/247 |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 5,800,414 A * | 9/1998 | Cazal .................. A61M 25/00 604/264 |
| 5,827,246 A * | 10/1998 | Bowen ................ A61M 1/008 604/313 |
| 5,891,111 A * | 4/1999 | Ismael ............... A61M 25/003 604/541 |
| 5,947,953 A * | 9/1999 | Ash ................. A61M 25/0021 138/115 |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,790,945 B1 * | 9/2010 | Watson, Jr. ......... A61F 13/0203 602/43 |
| 8,864,728 B2 * | 10/2014 | Long ................ A61M 25/003 604/319 |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2004/0254528 A1 * | 12/2004 | Adams ................ A61M 25/00 604/96.01 |
| 2005/0107756 A1 | 5/2005 | McCraw |
| 2009/0234306 A1 * | 9/2009 | Vitaris ............... A61F 13/0216 604/304 |
| 2010/0069829 A1 * | 3/2010 | Hutchinson ....... A61F 13/00068 604/28 |
| 2010/0106106 A1 * | 4/2010 | Heaton ............. A61B 17/0057 604/290 |
| 2011/0054283 A1 * | 3/2011 | Shuler ................ A61M 1/0088 600/364 |
| 2011/0230849 A1 * | 9/2011 | Coulthard ........... A61F 13/0216 604/319 |
| 2011/0276022 A1 * | 11/2011 | O'Day ................ A61M 25/0021 604/500 |
| 2011/0295190 A1 * | 12/2011 | David ..................... A61L 15/46 604/20 |
| 2014/0163532 A1 * | 6/2014 | Cornet .............. A61M 25/0071 604/543 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |

(56) References Cited

FOREIGN PATENT DOCUMENTS

| DE | 29 504 378 U1 | 9/1995 |
|---|---|---|
| DE | 202012010776 U1 | 11/2012 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov, Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N. A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G, Živadinovi?, V. ?uki?, Ž, Maksimovi?, ?. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G, Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

(56) References Cited

OTHER PUBLICATIONS

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.
Extended European Search Report for Corresponding Application No. 20183641.8, dated Oct. 7, 2020.

* cited by examiner

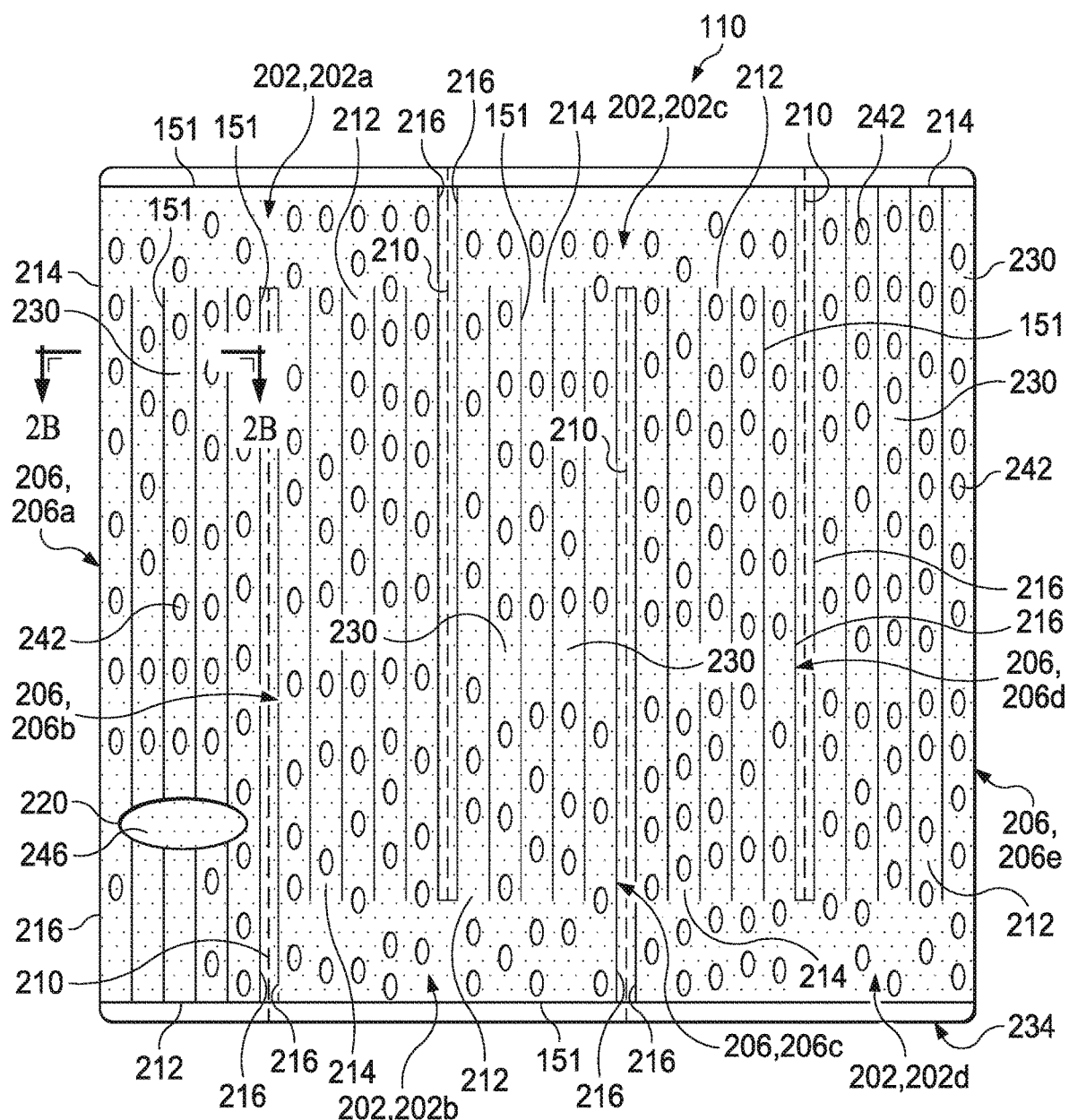
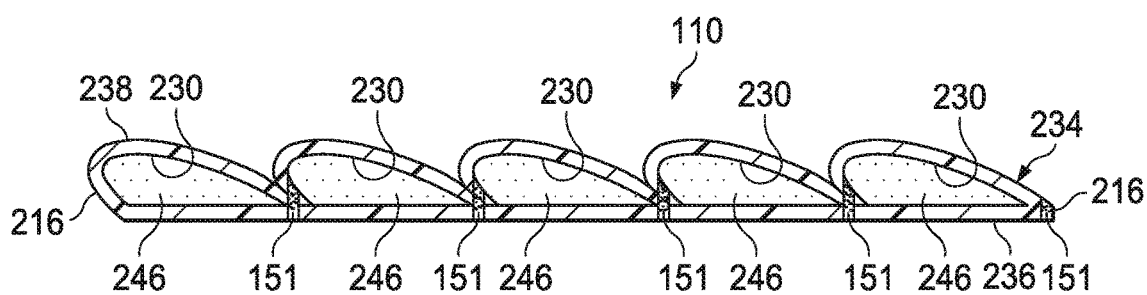
FIG. 2A
FIG. 2B

CUSTOMIZABLE CLOSED TISSUE SITE DRESSING FOR IMPROVED POSTOPERATIVE REMOVAL

RELATED APPLICATION

This application claims the benefit, under 35 USC 119(e), of the filing of U.S. Provisional Patent Application No. 62/110,870, entitled "Customizable Closed Tissue Site Dressing for Improved Postoperative Removal," filed Feb. 2, 2015, which is incorporated herein by reference for all purposes.

FIELD

This disclosure relates generally to medical treatment systems and, more particularly, but not by way of limitation, to systems, dressings, devices, and methods that may be suitable for treating a tissue site.

BACKGROUND

Depending on the medical circumstances, reduced pressure may be used for, among other things, reduced-pressure therapy to encourage granulation at a tissue site, draining fluids at a tissue site, closing a wound, reducing edema, promoting perfusion, and fluid management. Challenges can exist with extracting fluids from a tissue site under reduced-pressure therapy. For example, tissue sites may vary in volume, size, geometry, orientation, and other factors. Further, access to these tissue sites may be restricted. These and other factors can make extraction of waste fluids from the tissue site difficult to perform.

Types of tissue sites that may present particular difficulties may include locations such as a peritoneal cavity, and more generally, an abdominal cavity. For example, the abdominal cavity can be prone to complications such as peritonitis, abdominal compartment syndrome, and infections that can inhibit healing. Thus, improvements to treatment systems that may adapt to various types of tissue sites and orientations, reduce the invasiveness of the treatment, and increase efficiency and healing times may be desirable.

SUMMARY

In some illustrative embodiments, a system for treating a tissue site may include a fluid hub, a plurality of elongate fluid members, a separable joint, a pneumatic connector, and a reduced-pressure source. The plurality of elongate fluid members may be positioned in fluid communication with the fluid hub. Each of the plurality of elongate fluid members may include a proximal end, a distal end, and an elongate side between the proximal end and the distal end. The elongate side of the plurality of elongate fluid members may extend longitudinally outward from the fluid hub. The separable joint may be coupled between the elongate side of one of the plurality of elongate fluid members and the elongate side of another of the plurality of elongate fluid members. The pneumatic connector may be positioned in fluid communication with the plurality of elongate fluid members. The reduced-pressure source may be adapted to be positioned in fluid communication with the pneumatic connector.

In some illustrative embodiments, a dressing for treating a tissue site may include a fluid hub, a plurality of elongate fluid members, and a separable joint. The plurality of elongate fluid members may be positioned in fluid communication with the fluid hub. Each of the plurality of elongate fluid members may include a proximal end, a distal end, and an elongate side between the proximal end and the distal end. The elongate side of the elongate fluid members may extend longitudinally outward from the fluid hub. The separable joint may be coupled between the elongate side of one of the plurality of elongate fluid members and the elongate side of another of the plurality of elongate fluid members.

In some illustrative embodiments, a dressing for treating a tissue site may include a fluid hub, a first elongate fluid member, a second elongate fluid member, a separable joint, and a pneumatic connector. The first elongate fluid member may include a first proximal end, a first distal end, and a first elongate side defined between the first proximal end and the first distal end. The first distal end may be coupled in fluid communication to the fluid hub. The second elongate fluid member may include a second proximal end, a second distal end, and a second elongate side defined between the second proximal end and the second distal end. The second proximal end may be coupled in fluid communication to the fluid hub. The separable joint may be coupled between the first elongate side and the second elongate side and may be configured to releasably couple the first elongate side to the second elongate side. The pneumatic connector may be coupled in fluid communication at the first proximal end of the first elongate fluid member. Further, the pneumatic connector and the first proximal end of the first fluid member may be in fluid communication with the second distal end of the second fluid member through the fluid hub.

In some illustrative embodiments, a method for treating a tissue site may include providing a dressing. The dressing may include a plurality of elongate fluid members and a pneumatic connector. The plurality of elongate fluid members may include a proximal end, a distal end, and an elongate side between the proximal end and the distal end. The pneumatic connector may be positioned in fluid communication with the plurality of elongate fluid members. Further, the method may include positioning the plurality of elongate fluid members across the tissue site, and positioning the pneumatic connector through an external opening of the tissue site. Further, the method may include moving a fluid from the tissue site along the plurality of elongate fluid members to the pneumatic connector, and extracting the fluid through the pneumatic connector. Further, the method may include removing the plurality of elongate fluid members from the tissue site through the external opening by applying a removal force to the pneumatic connector.

In some illustrative embodiments, a method for removing a dressing from a tissue site may include providing the dressing positioned at the tissue site. The dressing may include a plurality of elongate fluid members, a pneumatic connector, and a separable joint. The plurality of elongate fluid members may include a proximal end, a distal end, and an elongate side between the proximal end and the distal end. The plurality of elongate fluid members may be positioned across the tissue site. The pneumatic connector may be positioned in fluid communication with the plurality of elongate fluid members. The pneumatic connector may extend through an external opening of the tissue site. The separable joint may be coupled between the elongate side of one of the plurality of elongate fluid members and the elongate side of another of the plurality of elongate fluid members. Further, the method may include removing the plurality of elongate fluid members from the tissue site through the external opening by applying a removal force to the pneumatic connector.

In some illustrative embodiments, a method for placing a dressing at a tissue site may include providing a dressing. The dressing may include a plurality of elongate fluid members and a pneumatic connector. The plurality of elongate fluid members may include a proximal end, a distal end, and an elongate side between the proximal end and the distal end. The pneumatic connector may be positioned in fluid communication with the plurality of elongate fluid members. Further, the method may include positioning the plurality of elongate fluid members across the tissue site, and positioning the pneumatic connector through an external opening of the tissue site. Positioning the plurality of elongate fluid members across the tissue site may include spacing the elongate side of at least one of the elongate fluid members apart from the elongate side of another of the elongate fluid members.

Other aspects, features, and advantages of the illustrative embodiments will become apparent with reference to the drawings and detailed description that follow.

BRIEF DESCRIPTION OF THE DRAWINGS

FIG. 2A is a plan view of an illustrative embodiment of a dressing shown in the system of FIG. 1, depicting an illustrative embodiment of a plurality of elongate fluid members coupled to one another for positioning at the tissue site;

FIG. 2B is a cross-section of the dressing of FIG. 2A, taken along line 2B-2B in FIGS. 1 and 2A;

DETAILED DESCRIPTION OF ILLUSTRATIVE EMBODIMENTS

In the following detailed description of non-limiting, illustrative embodiments, reference is made to the accompanying drawings that form a part hereof. Other embodiments may be utilized, and logical, structural, mechanical, electrical, and chemical changes may be made without departing from the scope of the appended claims. To avoid detail not necessary to enable those skilled in the art to practice the embodiments described herein, the description may omit certain information known to those skilled in the art. The following detailed description is non-limiting, and the scope of the illustrative embodiments are defined by the appended claims. As used herein, unless otherwise indicated, "or" does not require mutual exclusivity.

Figure 1:
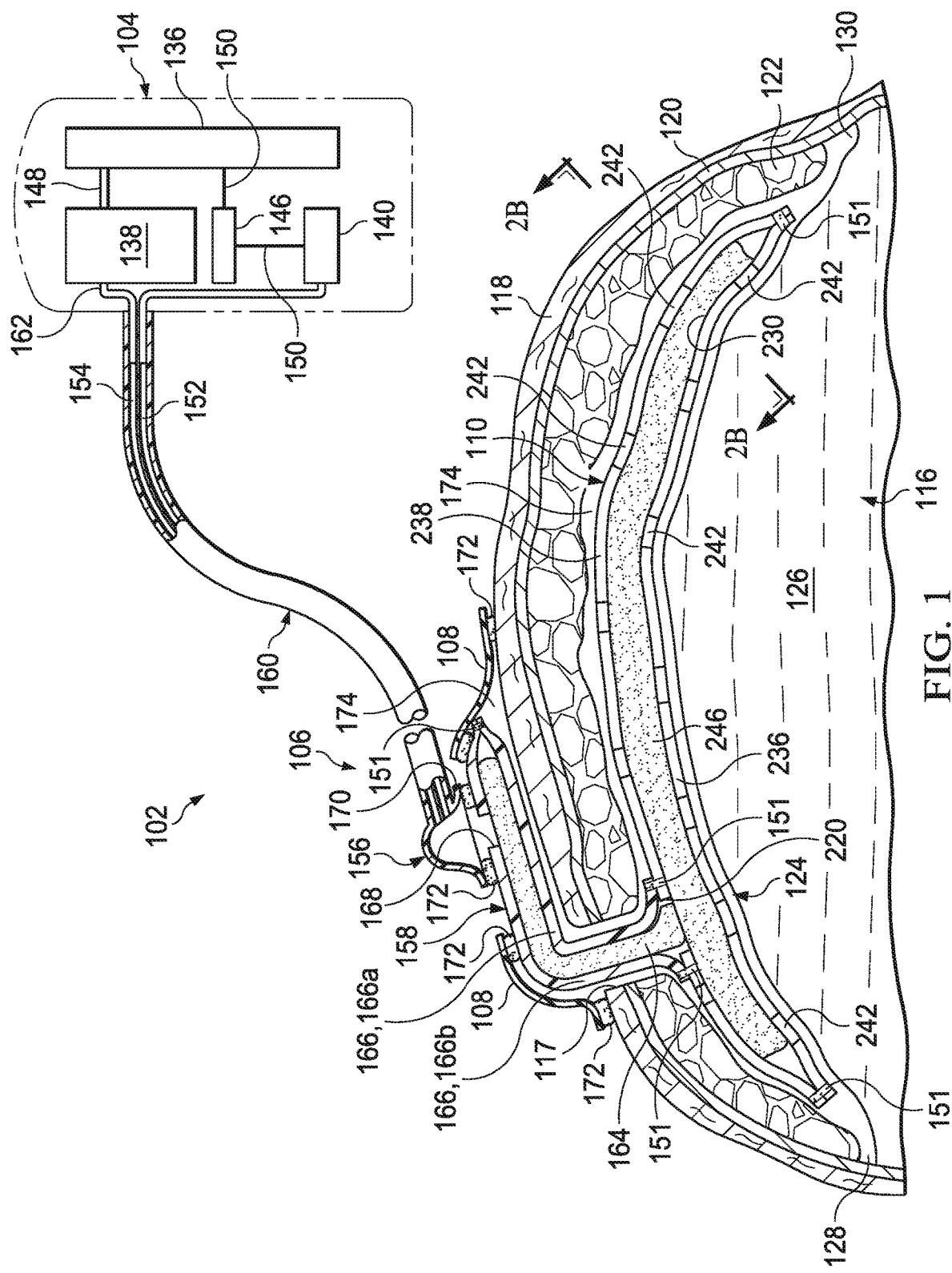
FIG. 1 is a partial cut-away view of an illustrative embodiment of a system for treating a tissue site deployed at an illustrative tissue site.

Referring to FIG. 1, in some illustrative embodiments, a system 102 may include a therapy device 104, a pneumatic connector 106, a sealing member 108, and a dressing 110. In other embodiments, components of the system 102 may be omitted or added as appropriate for specific applications. The system 102 may be suitable for providing reduced pressure treatment at a tissue site 116.

The tissue site 116 may be may be the bodily tissue of any human, animal, or other organism, including bone tissue, adipose tissue, muscle tissue, dermal tissue, connective tissue, cartilage, tendons, ligaments, or any other tissue. The tissue site 116 may extend through or otherwise involve an epidermis 118, a dermis 120, and a subcutaneous tissue 122. In some embodiments, the tissue site 116 may be a subsurface tissue site as depicted in FIG. 1 that extends below the surface of the epidermis 118. An external opening 117 may extend between the tissue site 116 and an exterior of the tissue site 116 to permit, without limitation, connection, placement, operation, or removal of components of the system 102. In other embodiments, the tissue site 116 may be a surface tissue site (not shown) that predominantly resides on a surface of the epidermis 118.

As shown in FIG. 1, the tissue site 116 may include tissue in a body cavity such as, without limitation, an abdominal cavity 124. The abdominal cavity 124 may include abdominal contents 126 or other tissue proximate the abdominal cavity 124. The dressing 110 may be disposed in the abdominal cavity 124 and supported on a surface of the abdominal contents 126. The dressing 110 may also be positioned in or proximate to a left lateral or first paracolic gutter 128 and a right lateral or second paracolic gutter 130. The first paracolic gutter 128 and the second paracolic gutter 130 may each be, for example, an open space on opposing sides of the abdominal cavity 124 among the abdominal contents 126. The first paracolic gutter 128 may be laterally disposed from the second paracolic gutter 130 or otherwise positioned on an opposite side of the tissue site 116 from the second paracolic gutter 130. The pneumatic connector 106 may be adapted to be positioned at the external opening 117 of the tissue site 116, for example, extending into the abdominal cavity 124. In some embodiments, the pneumatic connector 106 may be adapted to extend through the external opening 117. Although FIG. 1 depicts the system 102 deployed at the abdominal cavity 124, the system 102 may be used without limitation at other types of tissue sites. Further, the treatment of the tissue site 116 may include, without limitation, the removal of fluids, such as ascites and exudates, reduced-pressure therapy, instillation or distribution of fluids to the tissue site 116, and protection of the tissue site 116.

The therapy device 104 may be adapted to be positioned or coupled in fluid communication with the pneumatic connector 106 and the dressing 110. In some illustrative embodiments, the therapy device 104 may include a reduced-pressure source 136 and a canister 138. Further, in some embodiments, the therapy device 104 may optionally include and a sensor 140 and a controller 146. The components of the therapy device 104 may be arranged or associated with one another as shown in FIG. 1 to form the therapy device 104. However, in other embodiments (not shown), the components of the therapy device 104 may be provided separately or independently from the therapy device 104. Further, components of the therapy device 104 may be added or omitted as desired for a particular application.

The reduced-pressure source 136 may be adapted to be positioned or coupled in fluid communication with the pneumatic connector 106 and the dressing 110. In some embodiments, the reduced-pressure source 136 may be a pump, such as a portable pump. In other embodiments, the reduced-pressure source 136 may be any suitable device for providing reduced pressure, such as, for example, a wall suction source, a hand pump, or other source.

The canister 138 may be positioned in fluid communication between the reduced-pressure source 136 and the pneumatic connector 106. For example, the reduced-pressure source 136 may be positioned in fluid communication with the pneumatic connector 106 and the dressing 110 through the canister 138 such that fluid from the tissue site 116 and the dressing 110 maybe drawn into the canister 138. The canister 138 may be in fluid communication with a reduced-pressure inlet 148 of the reduced pressure source 136. The canister 138 may be any suitable containment device for holding or communicating fluids.

The sensor 140 may be, without limitation, a pressure sensor, a temperature sensor, or other sensor. The controller 146 may be, for example, a processor or similar device configured to control components of the therapy device 104, and to monitor the treatment or state of the tissue site 116. The controller 146 may be electrically coupled in any suitable manner to the reduced-pressure source 136, the sensor 140, or other components of the therapy device 104. For example, electrical conductors 150 may electrically couple the controller 146 to the reduced-pressure source 136 and the sensor as shown in FIG. 1. The controller 146 may include software or user programmable settings for controlling components of the therapy device 104 in relation to one another. For example, the controller 146 may control reduced pressure output from the reduced-pressure source 136 according to a signal generated or received from the sensor 140. The signal from the sensor 140 may be, for example, a pressure signal, a temperature signal, or other signal.

Reduced pressure may be applied to the tissue site 116 from the reduced-pressure source 136 to promote removal of ascites, exudates, or other fluids from the tissue site 116. Further, reduced pressure may be applied to stimulate the growth of additional tissue. In the case of a wound at the tissue site 116, the growth of granulation tissue, removal of exudates, or removal of bacteria may promote healing. In the situation of a non-wounded or non-defective tissue, reduced pressure may promote the growth of tissue that may be harvested and transplanted to another tissue site.

As used herein, "reduced pressure" may refer to a pressure less than the ambient pressure at a tissue site subject to treatment. In some embodiments, the reduced pressure may be less than the atmospheric pressure. The reduced pressure may also be less than a hydrostatic pressure at a tissue site. Unless otherwise indicated, values of pressure stated herein are gauge pressures. The reduced pressure delivered may be a constant pressure, varied pressure, intermittent pressure, or continuous pressure. Although the terms "vacuum" and "negative pressure" may be used to describe the pressure applied to a tissue site, the actual pressure applied to the tissue site may be more than the pressure normally associated with a complete vacuum. An increase in reduced pressure may correspond to a reduction in pressure (more negative relative to ambient pressure), and a decrease in reduced pressure may correspond to an increase in pressure (less negative relative to ambient pressure). While the amount and nature of reduced pressure applied to a tissue site may vary according to the application, in some embodiments, the reduced pressure may be between about −5 mm Hg to about −500 mm Hg. In other embodiments, the reduced pressure may be between about −100 mm Hg to about −200 mm Hg. In yet other embodiments, the reduced pressure may be between about −50 mm Hg to about −300 mm Hg.

Further, in some embodiments, components of the system 102, such as, without limitation, the reduced-pressure source 136, the therapy device 104, or the controller 146, may include preset selectors for an amount of reduced pressure, such as, for example, −100 mm Hg, −125 mm Hg, and −150 mm Hg. Further, the system 102 may also include a number of alarms, such as, for example, a blockage alarm, a leakage alarm, or a battery-low alarm.

Continuing with FIG. 1, the pneumatic connector 106 may be adapted to be accessible at the external opening 117 of the tissue site 116 to permit, for example, removal of the dressing 110 from the tissue site 116. In some embodiments, the pneumatic connector 106 may be directly coupled, secured, or tethered to the dressing 110, for example, by a weld 151, to permit removal of the dressing 110 from the tissue site 116 by the pneumatic connector 106. In some embodiments, the pneumatic connector 106 may be directly coupled to the dressing 110 with an adhesive or any suitable coupling device. The weld 151, adhesive, or other coupling device may also be used as described herein for coupling other components of the system 102. In some embodiments, a portion or more of the pneumatic connector 106 may be formed integrally with the dressing 110, or from a substrate material of the dressing 110.

The therapy device 104 may be in fluid communication with the dressing 110 through the pneumatic connector 106. In some illustrative embodiments, the pneumatic connector 106 may include a feedback lumen 152, a reduced-pressure lumen 154, a conduit interface 156, and a bridge 158. The pneumatic connector 106 may be supplied as part of the dressing 110, and components of the pneumatic connector 106 may be added, omitted, or used in any suitable combination in other embodiments. For example, in some embodiments, the pneumatic connector 106 may comprise a tube, lumen, pipe, or conduit that may be directly coupled in fluid communication with the dressing 110 without the feedback lumen 152, the conduit interface 156, or the bridge 158. Further, the feedback lumen 152 and the reduced-pressure lumen 154 may be combined or formed as part of a multi-lumen conduit 160 as shown in FIG. 1. In other embodiments, the feedback lumen 152 and the reduced-pressure lumen 154 may be separate conduits, tubes, lumens, or pipes, for example.

The feedback lumen 152 may be positioned or coupled in fluid communication with the sensor 140 in any suitable manner, such as, without limitation, through tubing, piping, or connectors coupled with adhesives, bonding, welding, couplers, unions, or interference fit. Similarly, the reduced-pressure lumen 154 may be positioned or coupled in fluid communication with the reduced-pressure source 136 in any suitable manner, such as, without limitation, through tubing, piping, or connectors coupled with adhesives, bonding, welding, couplers, unions, or interference fit. For example, the reduced-pressure lumen 154 may be in fluid communication with the reduced-pressure source 136 through the canister 138. Thus, the canister 138 may have an outlet in fluid communication with the reduced-pressure inlet 148, and a canister inlet 162 in fluid communication with the reduced-pressure lumen 154 for delivering reduced pressure communicated from the reduced-pressure inlet 148 to the reduced-pressure lumen 154. The reduced-pressure source 136, the reduced-pressure lumen 154, and the canister 136 may be fluidly coupled to one another in any suitable manner, such as, without limitation, through tubing, piping, or connectors coupled with adhesives, bonding, welding, couplers, or interference fit. Further, in some embodiments, the reduced-pressure lumen 154 may have a length that is fluidly isolated from a length of the feedback lumen 152.

In some embodiments, the bridge 158 may include a bridge manifold 164 that may be surrounded or encapsulated by a bridge film 166. The bridge 158, including the bridge manifold 164 and the bridge film 166, may be adapted to communicate fluid between the therapy device 104 and the dressing 110. In some embodiments, the bridge film 166 may be comprised of, or formed entirely of, a liquid impermeable material. Further, in some embodiments, the bridge film 166 may comprise a non-adherent material, such as a medical drape, capable of inhibiting tissue from adhering to the bridge 158. In some embodiments, the bridge film 166 may comprise a breathable polyurethane film. Further, in some embodiments, bridge film 166 may comprise any of the materials recited below for the sealing member 108.

In some embodiments, the bridge film 166 may include a first bridge film 166a and a second bridge film 166b. The bridge manifold 164 may be surrounded between the first bridge film 166a and the second bridge film 166b. The first bridge film 166a may be sealingly coupled to the second bridge film 166b in any suitable manner, such as, for example, by the weld 151. Although not shown in FIG. 1, the weld 151, or other coupling device, may be positioned around the perimeter of the bridge manifold 164 or at the edges of the bridge manifold 164. Similar to the bridge film 166, the first bridge film 166a and the second bridge film 166b may be comprised of a liquid impermeable material or any of the materials recited or referenced above for the bridge film 166. A bridge aperture 168 may be disposed through the bridge film 166 in fluid communication with the bridge manifold 164.

The bridge manifold 164 may be formed from any manifold material or flexible bolster material that provides a vacuum space, or treatment space, such as, for example, a porous and permeable foam or foam-like material, a member formed with pathways, a graft, or a gauze. In some embodiments, any material or combination of materials may be used as a manifold material for the bridge manifold 164 provided that the manifold material is operable to distribute or collect fluid across a tissue site. For example, the term manifold may refer to a substance or structure capable of delivering fluids to or removing fluids from across a tissue site through a plurality of pores, pathways, or flow channels. The plurality of pores, pathways, or flow channels may be interconnected to improve distribution of fluids provided to and removed from an area around the manifold. Examples of such manifolds may include, without limitation, devices that have structural elements arranged to form flow channels, cellular foam, such as open-cell foam, porous tissue collections, and liquids, gels, and foams that include or cure to include flow channels. Further, the bridge manifold 164 may be biocompatible. In some embodiments, the bridge manifold 164 may comprise a porous, hydrophobic material. In such an embodiment, the hydrophobic characteristics of the bridge manifold 164 may prevent the bridge manifold 164 from directly absorbing fluid, but may allow the fluid to pass through.

In some embodiments, the bridge manifold 164 may be a reticulated, open-cell polyurethane or polyether foam that is fluid permeable. One such material may be the VAC® GranuFoam® material available from Kinetic Concepts, Inc. of San Antonio, Tex. However, a material with a higher or lower density than GranuFoam® material may be desirable for the manifold 180 depending on the application. Among the many possible materials, the following may be used without limitation: GranuFoam® material; Foamex® technical foam (www.foamex.com); LIBELTEX DRY WEB; LIBELTEX TDL2; LIBELTEX TL4; a molded bed of nails structure; a patterned grid material, such as those manufactured by Sercol Industrial Fabrics; 3D textiles, such as those manufactured by Baltex of Derby, U.K.; a mass of filaments that may be adapted to provide a laminar fluid flow; a unidirectional manifold structure, such as a bundle of longitudinal filaments; a bundle of longitudinal filaments oriented substantially collinear to a desired direction of fluid flow; an array of polyamide monofilaments; a gauze; a flexible channel-containing member; and a graft.

In other embodiments, the bridge manifold 164 may comprise a material including closed cells. The closed cells may not be fluidly connected to adjacent cells in the bridge manifold 164. The closed cells may be selectively disposed in the bridge manifold 164 to, for example, prevent transmission of fluids through perimeter surfaces of the manifold 164. Other layers may be included in or on the bridge manifold 164, such as absorptive materials, wicking materials, hydrophobic materials, and hydrophilic materials. In some embodiments, the bridge manifold 164 may be enhanced with ionic silver and anti-microbial agents.

The conduit interface 156 may be any suitable connector, such as a coupling that may be molded, machined, formed or adapted in any suitable manner for providing fluid communication among components of the system 102. For example, as shown in FIG. 1, the conduit interface 156 may be adapted to fluidly couple the bridge 158 to the feedback lumen 152 and the reduced-pressure lumen 154. However, in other embodiments, the conduit interface 156 may be directly coupled to the dressing 110 without the bridge 158. In yet other embodiments, the conduit interface 156 may be coupled to the reduced-pressure lumen 154 without the feedback lumen 152. Other embodiments are possible.

In some embodiments, the conduit interface 156 may include a flange 170 surrounding or positioned around an inlet of the conduit interface 156. The inlet of the conduit interface 156 may be in fluid communication with an outlet of the conduit interface 156 that may be adapted to be fluidly coupled to the feedback lumen 152 and the reduced-pressure lumen 154. The flange 170 may be adapted to be coupled to a component of the system 102, such as the bridge 158 or the dressing 110, for example, with an adhesive 172 or other coupling device. The adhesive 172 may be adapted to be positioned between the flange 170 and the bridge 158 or the dressing 110. For example, the flange 170 may be positioned about the bridge aperture 168 and coupled to a surface of the bridge 158 with the adhesive 172 to provide fluid communication among the inlet of the conduit interface 156, the bridge manifold 164, and the dressing 110. The adhesive 172 may also be used with other components of the system 102. In other embodiments, the conduit interface 156 may be positioned or coupled in fluid communication with components of the system 102 in any suitable manner, such as, without limitation, through tubing, piping, or connectors coupled with adhesives, bonding, welding, couplers, unions, or interference fit.

The sealing member 108 may be adapted to cover at least a portion of the dressing 110 and the tissue site 116, and to provide a fluid seal and a sealed space 174 about the tissue site 116 or between the sealing member 108 and the tissue site 116. A portion of the sealing member 108 may overlap or cover tissue surrounding the tissue site 116, such as the epidermis 118. The dressing 110 and a portion of the pneumatic connector 106, such as the bridge 158, may be sized or otherwise adapted to be positioned in the sealed space 174, and may be secured at the external opening 117 of the tissue site 116. The external opening 117 may provide access to the tissue site 116 from an exterior of the tissue site 116. The sealing member 108 may provide a fluid seal, for example, at, over, or covering the external opening 117.

The sealing member 108 may be formed from any material that may allow for a fluid seal, such as, for example, a liquid impermeable material. A fluid seal may be a seal adequate to maintain reduced pressure, if applicable, at a desired site. The sealing member 108 may comprise, for example, one or more of the following materials: hydrophilic polyurethane; cellulosics; hydrophilic polyamides; polyvinyl alcohol; polyvinyl pyrrolidone; hydrophilic acrylics; hydrophilic silicone elastomers; an INSPIRE 2301 material from Expopack Advanced Coatings of Wrexham, United Kingdom having, for example, a moisture vapor transmission rate or MVTR (inverted cup technique) of 14400 g/m2/24 hours and a thickness of about 30 microns; a thin, uncoated polymer drape; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; polyurethane (PU); EVA film; co-polyester; silicones; a silicone drape; a 3M Tegaderm® drape; a polyurethane (PU) drape such as one available from Avery Dennison Corporation of Pasadena, Calif.; polyether block polyamide copolymer (PEBAX), for example, from Arkema, France; EXPOPACK 2327; or other appropriate material.

The sealing member 108 may be vapor permeable and liquid impermeable, thereby allowing vapor and inhibiting liquids from exiting the sealed space 174. In some embodiments, the sealing member 108 may be a flexible, breathable film, membrane, or sheet having a high MVTR of, for example, at least about 300 g/m2 per 24 hours. The use of a high MVTR material for the sealing member 108 may permit moisture vapor to pass through the sealing member 108, external to the sealed space 174, while maintaining the fluid seal described above. In other embodiments, a low or no vapor transfer drape might be used. In some embodiments, the sealing member 108 may comprise a range of medically suitable films having a thickness between about 15 microns (μm) to about 50 microns (μm).

In some embodiments, the adhesive 172, or other attachment device, may be adapted to be positioned between the sealing member 108 and the tissue site 116. For example, the adhesive 172 may be positioned on or applied to an interior facing side of the sealing member 108 for facing the tissue site 116. In some embodiments, the sealing member 108 may be sealed directly against tissue surrounding the tissue site 116, such as the epidermis 118, by the adhesive 172. In other embodiments, the adhesive 172 may seal the sealing member 108 against a gasket or drape (not shown) adapted to be positioned between the adhesive 172 and the epidermis 118.

The adhesive 172 may be a medically-acceptable adhesive and may take numerous forms, such as an adhesive sealing tape, drape tape, paste, hydrocolloid, hydrogel, or other suitable sealing device. The adhesive 172 may also be flowable. Further, the adhesive 172 may comprise, without limitation, an acrylic adhesive, rubber adhesive, high-tack silicone adhesive, polyurethane, or other adhesive substance. In some embodiments, the adhesive 172 may be a pressure-sensitive adhesive comprising an acrylic adhesive with coat weight, for example, of about 15 grams/m2 (gsm) to about 70 grams/m2 (gsm). In some embodiments, the adhesive 172 may be continuous or discontinuous.

Referring to FIG. 2A, in some illustrative embodiments, the dressing 110 may include a fluid hub 202, a plurality of elongate fluid members 206, and a separable joint 210. The elongate fluid members 206 may be positioned in fluid communication with the fluid hub 202. Each of the elongate fluid members 206 may include a proximal end 212, a distal end 214, and an elongate side 216 between the proximal end 212 and the distal end 214. The elongate side 216 may extend longitudinally outward from the fluid hub 202. Further, the elongate side 216 may be positioned normal relative to the proximal end 212 and the distal end 214 of the elongate fluid members 206.

The separable joint 210 may be coupled between the elongate side 216 of one of the elongate fluid members 206 and the elongate side 216 of another of the elongate fluid members 206. The separable joint 210 may be configured to releasably couple the elongate side 216 of one of the elongate fluid members 206 to the elongate side 216 of another of the elongate fluid members 206. The separable joint 210 may extend longitudinally outward from the fluid hub 202, and may be positioned along or substantially parallel to one or more of the elongate sides 216. Further, the separable joint 210 may extend from the fluid hub 202 to an outer edge or periphery of the dressing 110 to facilitate separation of the elongate fluid members 206 from one another at the outer edge and along one or more of the elongate sides 216. The separable joint 210 may intersect the outer edge or periphery of the dressing 110 to facilitate the separation of the elongate fluid members 206 from one another. In some embodiments, the separable joint 210 may comprise perforations between adjacent elongate fluid members 206. In other embodiments, the separable joint 210 may comprise a score or other device adapted to enhance separation of the elongate fluid members 206 from one another.

In some embodiments, the dressing 110 may include the pneumatic connector 106 shown in FIG. 1. The pneumatic connector 106 may be positioned or coupled in fluid communication with the dressing 110 and the elongate fluid members 206 through a dressing aperture 220. For example, the bridge 158 may be coupled in fluid communication with the dressing 110 at or about the dressing aperture 220. The dressing aperture 220 may be disposed through a portion of the dressing 110 and in fluid communication with the contents of the dressing 110. Further, the pneumatic connector 106 may be coupled to at least one of the elongate fluid members 206 and adapted to be accessible at the external opening 117 of the tissue site 116, for example, to permit removal of the elongate fluid members 206 from the tissue site 116.

Continuing with FIG. 2A, the fluid hub 202 and the elongate fluid members 206 may be adapted to communicate or distribute fluid throughout the dressing 110. The fluid hub 202 may provide fluid communication between and among the elongate fluid members 206. The fluid hub 202 may be positioned or coupled in fluid communication with the elongate fluid members 206 in various configurations. For example, as shown in FIG. 2A, the fluid hub 202 may be formed integrally with the elongate fluid members 206, or from a portion of a substrate material of the elongate fluid members 206 or the dressing 110. Further, as shown in FIG. 2A, the fluid hub 202 may be free of the welds 151 and the separable joint 210. In other embodiments, the fluid hub 202 may be a joint, coupling, or similar connecting device in fluid communication between the elongate fluid members 206. Examples of various configurations are described in the following illustrative embodiments.

Each of the elongate fluid members 206 may be adapted to communicate fluid between the proximal end 212 and the distal end 214 thereof. In some embodiments, the proximal end 212 or the distal end 214 of the elongate fluid members 206 may be coupled to the fluid hub 202. For example, as shown in FIG. 2A, in some embodiments, the plurality of elongate fluid members 206 may include a first elongate fluid member 206a, a second elongate fluid member 206b, a third elongate fluid member 206c, a fourth elongate fluid member 206d, and a fifth elongate fluid member 206e. Further, in some embodiments, the fluid hub 202 may be a first fluid hub 202a and the dressing 110 may additionally include a second fluid hub 202b, a third fluid hub 202c, and a fourth fluid hub 202d. Although five of the elongate fluid members 206 and four of the fluid hubs 202 are shown in FIG. 2A, the dressing 110 may include any number of the elongate fluid members 206 and the fluid hubs 202 as desired.

In some embodiments, the distal end 214 of the first elongate fluid member 206a may be fluidly coupled to the first fluid hub 202a. Further, the proximal end 212 of the second elongate fluid member 206b may be fluidly coupled to the first fluid hub 202a. The proximal end 212 of the first elongate fluid member 206a may be in fluid communication with the distal end 214 of the second elongate fluid member 206b through the first fluid hub 202a. In some embodiments, the pneumatic connector 106 may be fluidly coupled at the proximal end 212 of the first elongate fluid member 206a. Thus, the pneumatic connector 106 may provide fluid communication through or along the length of both the first elongate fluid member 206a and the second elongate fluid member 206b. In other embodiments, the pneumatic connector 106 and the fluid hub 202 may each be fluidly coupled to opposite ends of one of the elongate fluid members 206.

Additional elongate fluid members 206 may be added in an analogous manner. For example, the distal end 214 of the second elongate fluid member 206b may be fluidly coupled to the second fluid hub 202b. Further, the proximal end 212 of the third elongate fluid member 206c may be fluidly coupled to the second fluid hub 202b. The proximal end 212 of the second elongate fluid member 206b may be in fluid communication with the distal end 214 of the third elongate fluid member 206c through the second fluid hub 202b. Adding additional elongate fluid members 206, the distal end 214 of the third elongate fluid member 206c may be fluidly coupled to the third fluid hub 202c. Further, the proximal end 212 of the fourth elongate fluid member 206d may be fluidly coupled to the third fluid hub 202c. The proximal end 212 of the third elongate fluid member 206c may be in fluid communication with the distal end 214 of the fourth elongate fluid member 206d through the third fluid hub 202c. Adding yet additional elongate fluid members 206, the distal end 214 of the fourth elongate fluid member 206d may be fluidly coupled to the fourth fluid hub 202d. Further, the proximal end 212 of the fifth elongate fluid member 206e may be fluidly coupled to the fourth fluid hub 202d. The proximal end 212 of the fourth elongate fluid member 206d may be in fluid communication with the distal end 214 of the fifth elongate fluid member 206e through the fourth fluid hub 202d.

Thus, the pneumatic connector 106 may be fluidly coupled at the proximal end 212 of the first elongate fluid member 206a and in fluid communication with the distal end 214 of the fifth elongate fluid member 206e through the length of each of the elongate fluid members 206a, 206b, 206c, 206d, 206e. Thus, in some embodiments, an end of one of the elongate fluid members 206 may be fluidly coupled to an end of another of the elongate fluid members 206 through the fluid hub 202. Further, in some embodiments, the elongate side 216 of the elongate fluid members 206 may be fluidly sealed to preclude fluid communication through the elongate side 216. Other embodiments are possible.

The fluid hub 202 and the plurality of elongate members 206 may be sized or adapted to be positioned at the tissue site 116. In embodiments of the tissue site 116 including the abdominal cavity 124, the fluid hub 202 may be positioned adjacent to, against, or supported by the abdominal contents 126, while the elongate fluid members 206 may be positioned at the first paracolic gutter 128 or the second paracolic gutter 130. Other embodiments are possible. Further, in some embodiments, more than one dressing 110 may be positioned at the tissue site 116 as desired. Further, the dressing 110 may be made visible at the tissue site 116 under X-ray, for example, by adding a radiopaque stripe or impregnating the dressing 110 with a radiopaque material such as barium.

Referring to FIGS. 2A-2B, in some embodiments, the elongate fluid members 206 may include at least one fluid lumen 230 positioned between the proximal end 212 and the distal end 214 thereof. In some embodiments, the fluid lumen 230 may be positioned longitudinally in fluid communication between the proximal end 212 and the distal end 214. Further, the fluid lumen 230 may extend substantially parallel to the elongate side 216 and the separable joint 210.

In some embodiments, the fluid lumen 230 may be defined by at least a portion of a dressing film 234. The dressing film 234 may be comprised of a liquid impermeable material. In some embodiments, the dressing film 234 may comprise a non-adherent material, such as a medical drape, which may be capable of inhibiting tissue from adhering to the dressing film 234. In some embodiments, the dressing film 234 may comprise a breathable polyurethane film. Further, in some embodiments, dressing film 234 may comprise any of the materials recited above for the sealing member 108.

In some embodiments, the dressing film 234 may include two outer layers, such as a first dressing film 236 and a second dressing film 238. The fluid lumen 230 may be defined between the first dressing film 236 and the second dressing film 238. For example, the first dressing film 236 may be folded or pleated with a bellows or accordion profile to form the fluid lumen 230, and coupled to the second dressing film 238 on opposing sides of the fluid lumen 230. The first dressing film 236 may be coupled to the second dressing film 238 in any suitable manner, such as, for example, by the weld 151. The weld 151 may be continuous or discontinuous, and may be positioned at the top and the bottom of the dressing 110 for the orientation shown in FIG. 2A. In other non-limiting embodiments, the first dressing film 236 may be coupled to the second dressing film 238 with other suitable coupling devices such as adhesives or cements. The first dressing film 236 and the second dressing film 238 may each be comprised of a liquid impermeable material, or any of the materials recited above for the dressing film 234.

Further, in some embodiments, a plurality of fenestrations 242 may be disposed through the dressing film 234. For example, the fenestrations 242 may be disposed through at least one of the first dressing film 236 and the second dressing film 238 in fluid communication with the fluid lumen 230.

In some embodiments, the fluid lumen 230 may carry at least of portion of a dressing manifold 246. The dressing manifold 246 may be disposed in the fluid lumen 230. Further, the dressing film 234, such as the first dressing film 236 and the second dressing film 238, may surround the dressing manifold 246. In some embodiments, the dressing manifold 246 may comprise foam or any of the materials recited above for the bridge manifold 164.

The pneumatic connector 106 may be in fluid communication with the fluid lumen 230 and the dressing manifold 246 through the dressing aperture 220. For example, the bridge manifold 164 of the bridge 158 may be positioned proximate to the dressing manifold 246 through the dressing aperture 220 and in fluid communication with the fluid lumen 230 and the dressing manifold 246. The dressing aperture 220 may be disposed through the first dressing film 236 or the second dressing film 238.

Continuing with FIGS. 2A-2B, the separable joint 210 may be, for example, carried by, positioned on, or disposed through a portion of the dressing film 234, such as the first dressing film 236 and the second dressing film 238. The first dressing film 236 may be coupled in any suitable manner to the second dressing film 238 around the separable joint 210 at the elongate side 216 of the elongate fluid members 206, for example, by the weld 151. In some embodiments, the weld 151 may be continuous or configured to sealingly couple the first dressing film 236 to the second dressing film 238. Thus, in some embodiments, the weld 151 may preclude fluid communication through the elongate sides 216 before and after separation of the elongate fluid members 206 from one another at the separable joint 210. In other embodiments, the weld 151 may be discontinuous or configured to permit fluid communication through the elongate sides 216.

Figure 3:
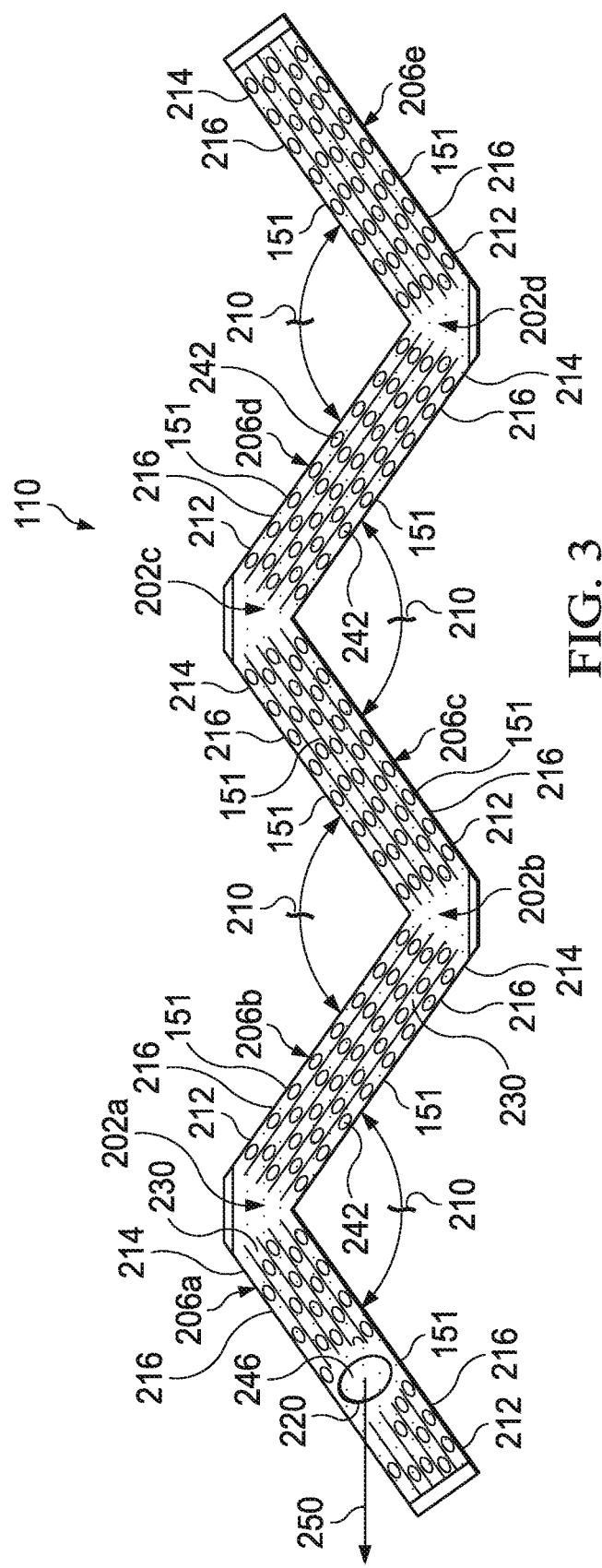
FIG. 3 is a plan view of the dressing of FIG. 2A, depicting the plurality of elongate members disconnected and separated from one another.

The separable joint 210 and the dressing 110 may be moveable from a coupled state to a separated state. FIG. 2A depicts the separable joint 210 and the dressing 110 in the coupled state with the elongate side 216 of the elongate fluid members 206 releasably coupled to one another. As illustrated in the example of FIG. 2A, some embodiments of the dressing 110 may include the elongate fluid members 206 coupled end-to-end through one or more of the fluid hubs 202, while the separable joint 210 retains the relative positions of the elongate fluid members 206 in the coupled state. For example, the separable joint 210 may retain the elongate fluid members 206 parallel to one another in a coupled state. FIG. 3 depicts the separable joint 210 and the dressing 110 in the separated state with the elongate side 216 of the elongate fluid members 206 released or separated from one another. In the separated state, the elongate fluid members 206 may be coupled to one another end-to-end, changing the shape or footprint of the dressing 110 to an elongate or ribbon-like shape, which can facilitate removal of the dressing 110 through a minimally invasive exit point.

Referring to FIG. 3, when the dressing 110 is positioned at the tissue site 116, for example, a pulling force 250 applied at the proximal end 212 of the first elongate fluid member 206a may separate at least one of the elongate fluid members 206 from another of the elongate fluid members 206, positioning the separable joint 210 in the separated state. The separable joint 210 may enhance the ability of the dressing 110 to cover a larger surface area at the tissue site 116. Further, the separable joint 210 may enhance removal of the dressing 110 from the tissue site 116 in a less invasive manner, for example, by changing the shape or footprint of the dressing 110 such that each of the elongate fluid members 206 may be removed from the tissue site 116 sequentially or one at a time. Such a configuration may provide for removal of the dressing 110 from the tissue site 116 through the external opening 117 without requiring further surgery, an additional incision, or re-opening of the tissue site 116 after the dressing 110 has been positioned at the tissue site 116 for treatment. For example, the pulling force 250 may be applied to the pneumatic connector 106 from exterior to the tissue site 116. The pneumatic connector 106 may transfer the pulling force 250 through the external opening 117 proximate to or about the dressing aperture 220, which may be positioned at the proximal end 212 of the first elongate fluid member 206a, thereby moving the separable joint 210 and the dressing 110 to the separated state.

Figure 4A:
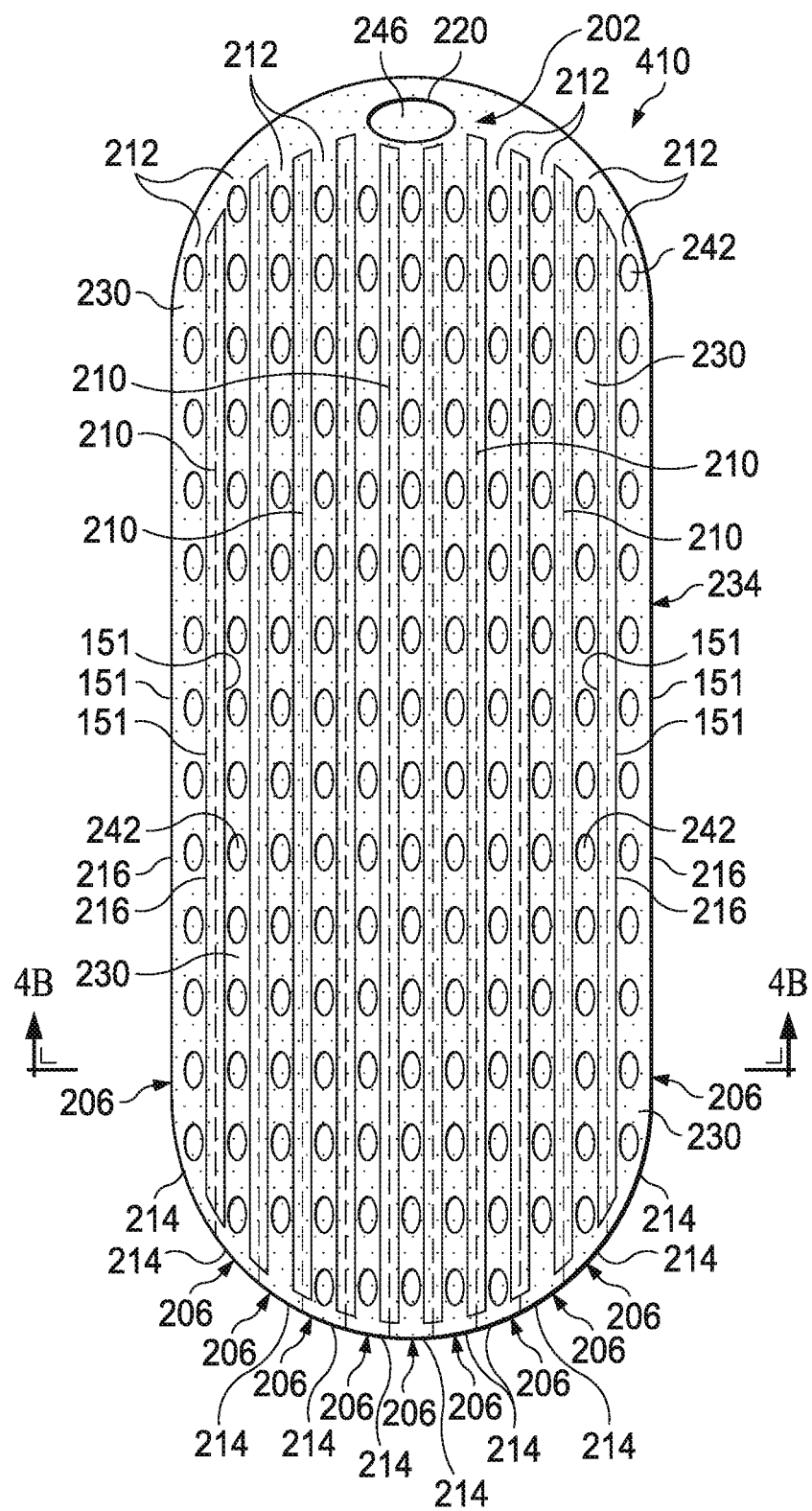
FIG. 4A is another illustrative embodiment of a dressing suitable for use with the system of FIG. 1.

Referring to FIG. 4A, depicted is another illustrative embodiment of a dressing 410 suitable for use with the system 102. Similar to the dressing 110, the dressing 410 may include the fluid hub 202, the plurality of elongate fluid members 206, and the separable joint 210. However, as shown in FIG. 4A, the proximal end 212 of each of the elongate fluid members 206 may be coupled to a single fluid hub 202. Further, each of the elongate fluid members 206 may use a single fluid lumen 230 as shown in FIG. 4. In other embodiments, each of the elongate fluid members 206 may include any number of the fluid lumens 230 as desired. Similar to the dressing 110, the dressing 410 may also include the dressing manifold 246 positioned in the fluid lumen 230 and the fluid hub 202 of the dressing 410.

The pneumatic connector 106, described above in FIG. 1, may be positioned or coupled in fluid communication with the dressing 410 and the elongate fluid members 206 through the dressing aperture 220. In the embodiment of FIG. 4A, the dressing aperture 220 and the pneumatic connector 106 may be positioned at the fluid hub 202. Thus, each of the elongate fluid members 206 may extend longitudinally outward from the fluid hub 202 and the pneumatic connector 106.

Figure 4B:
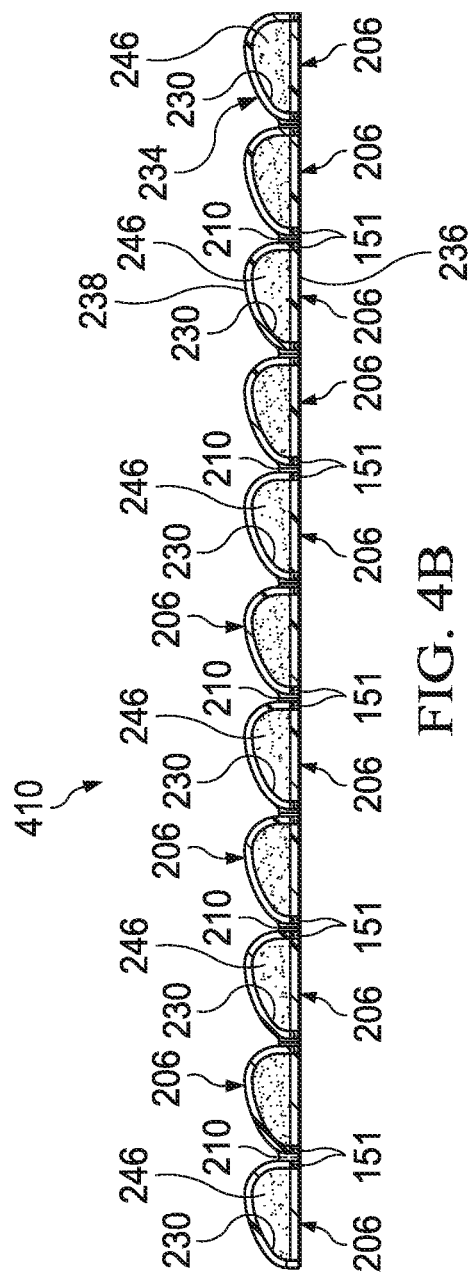
FIG. 4B is a cross-section of the dressing of FIG. 4A, taken along line 4B-4B in FIG. 4A.
Figure 5A:
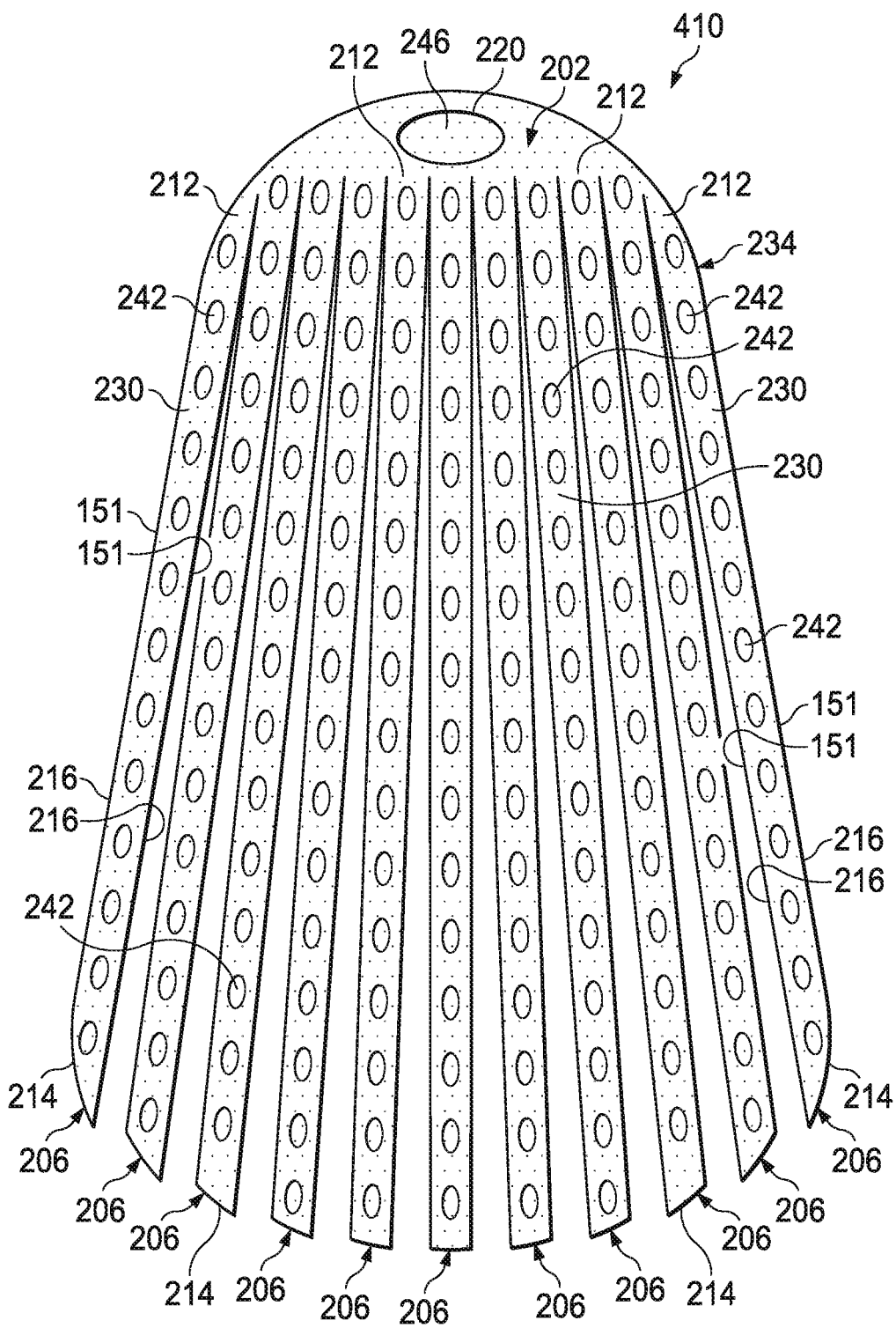
FIG. 5A is a plan view of the dressing of FIG. 4A, depicting the plurality of elongate members disconnected and separated from one another.

Referring to FIGS. 4A-4B, the dressing 410 may include the first dressing film 236 sealingly coupled to the second dressing film 238 around the separable joint 210 at the elongate side 216 of the elongate fluid members 206, for example, by the weld 151. FIGS. 4A and 4B depict the separable joint 210 and the dressing 410 in the coupled state with the elongate side 216 of the elongate fluid members 206 releasably coupled to one another. FIG. 5A depicts the separable joint 210 and the dressing 410 in the separated state with the elongate side 216 of the elongate fluid members 206 released or separated from one another. When the separable joint 210 of the dressing 410 is in the separated state, the distal end 214 of the elongate fluid members 206 may be moveable relative to one another and capable of fanning out into a mop-like shape. Such a configuration may permit the dressing 410 to be positioned at the tissue site 116 over a larger surface area, or provide for selective positioning of the elongate fluid members 206 in a desired location at the tissue site 116.

Figure 5B:
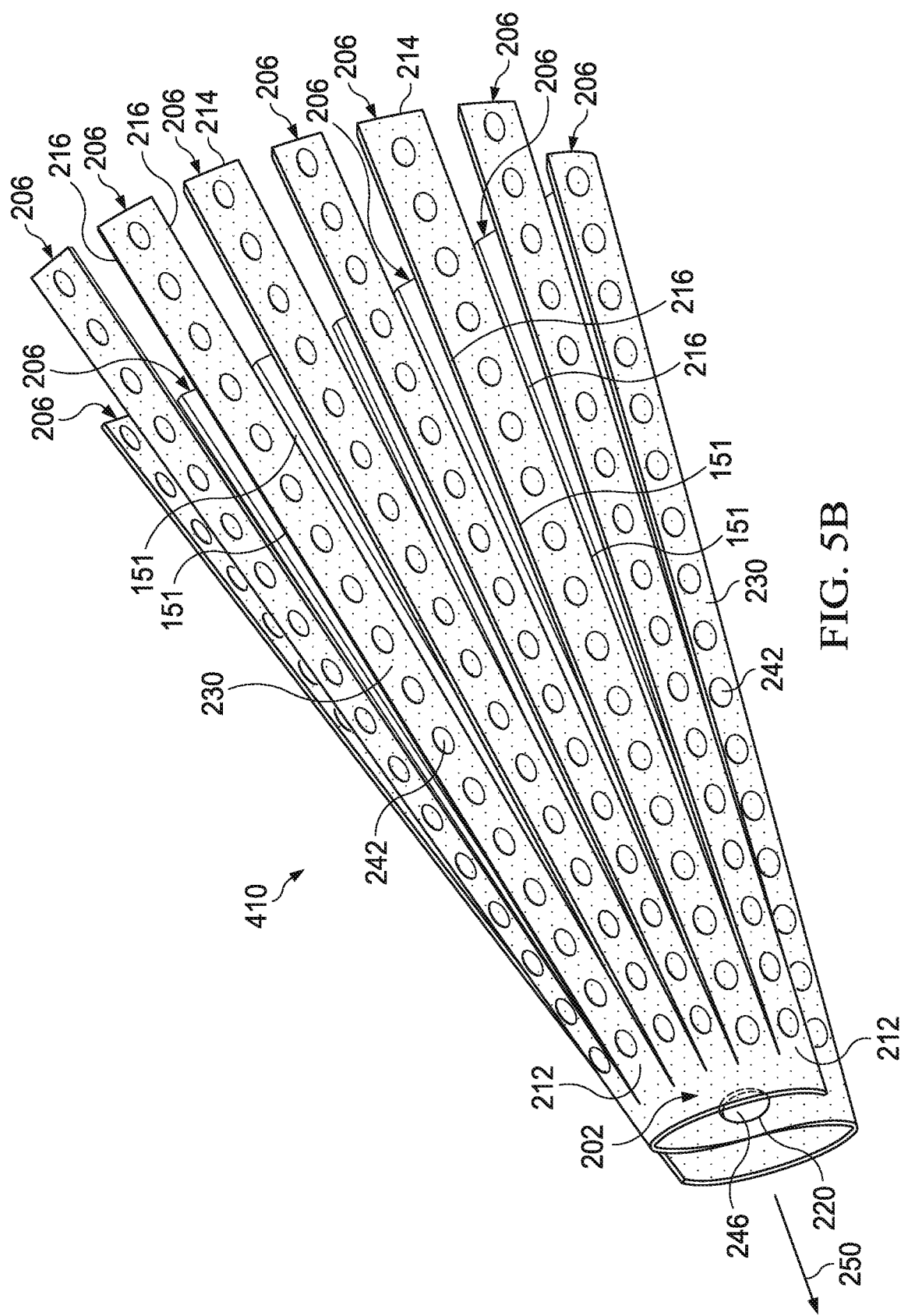
FIG. 5B is a perspective view of the dressing of FIG. 4A, depicting the plurality of elongate members disconnected from one another and gathered together for removal from the tissue site.

FIG. 5B depicts the pulling force 250 being applied at the fluid hub 202 of the dressing 410, illustrating the dressing 410 and the elongate fluid members 206 in a folded and gathered state suitable for removal from the tissue site 116 through the external opening 117. Such a configuration may enhance removal of the dressing 410 from the tissue site 116 in a less invasive manner, for example, without requiring further surgery or re-opening of the tissue site 116 after the dressing 410 has been positioned at the tissue site 116 for treatment. For example, the pulling force 250 may be applied to the pneumatic connector 106, coupled at the fluid hub 202, from exterior to the tissue site 116. The pneumatic connector 106 may transfer the pulling force 250 through the external opening 117 proximate to the fluid hub 202 and about the dressing aperture 220, positioning the dressing 410 and the elongate fluid members 206 in the folded and gathered state for removal.

Referring generally to FIGS. 1-5B, in some illustrative embodiments of operation of the system 102, the dressing 110, 410 may be disposed at or within the tissue site 116, such as the abdominal cavity 124. The dressing 110, 410 may be positioned adjacent to or in contact with the tissue site 116. In some embodiments, at least one of the elongate fluid members 206 of the dressing 110, 410 may be positioned in, proximate to, or in contact with the first paracolic gutter 128 or the second paracolic gutter 130. Further, in some embodiments, the elongate fluid members 206 may be positioned at the tissue site 116 with the elongate side 216 of the elongate fluid members 216 being coupled to one another. For example, the dressing 110, 410 may be positioned at the tissue site 116 in the coupled state described above.

In other embodiments, at least one of the elongate fluid members 206 may be separated from another of the elongate fluid members 206 prior to or during deployment of the dressing 110, 410 at the tissue site 116. In this manner, the elongate side 216 of at least one of the elongate fluid members 206 may be separated from the elongate side 216 of another of the elongate fluid members 206 and spread out or positioned across the tissue site 116 to cover a larger surface area, or a particular area that may be desired for treatment. Additional dressings 110, 410 may be used and positioned as desired, for example, on opposite sides of the abdominal contents 126. When deployed, the dressing 110, 410 may cover all exposed viscera and may separate the viscera from contact with the walls of the abdominal cavity 124. The dressing 110, 410 may be sized and shaped to permit such coverage.

The sealing member 108 may be positioned and fluidly sealed about the tissue site 116 with the adhesive 172 as described above. The tissue site 116 may be closed around the dressing 110, 410 to form the external opening 117. The pneumatic connector 106 may be accessible through the external opening 117 of the tissue site 116 for connection to the therapy device 104 or other components.

Activating the reduced-pressure source 136 may provide reduced pressure to the tissue site 116 through the pneumatic connector 106 and the dressing 110, 410. When the reduced-pressure source 136 is activated, the dressing 110, 410 may distribute the reduced pressure to the tissue site 116 through the fluid hub 202 and the elongate fluid members 206. The reduced pressure may be distributed to the tissue site 116 through the dressing apertures 242 that may be associated with the fluid hub 202 and the elongate fluid members 206, for example. Fluid from the tissue site 116 may be communicated from the dressing 110, 410 to the canister 138 through the pneumatic connector 106. When under reduced pressure, the dressing manifold 246 may keep the fluid lumen 230 open and in communication with the tissue site 116.

After the tissue site 116 has been closed around the dressing 110, 410, the dressing 110, 410 may be removed from the tissue site 116 post-operatively in a non-invasive or less invasive manner with minimal surgical implications. For example, the external opening 117 at the tissue site 116 may have a length or diameter greater than about 6 millimeters. In some embodiments, the external opening 117 may have a length or diameter between about 6 millimeters to about 10 millimeters, and in some embodiments, about 8 millimeters. The pneumatic connector 106 may be accessed through or at the external opening 117, and the dressing 110, 410 may be removed or pulled from the tissue site 116 by, for example, applying the pulling force 250 to the pneumatic connector 106 or other components of the dressing 110, 410 through the external opening 117.

Continuing generally with FIGS. 1-5B, further described are illustrative methods for treating the tissue site 116. In some illustrative embodiments, a method for treating the tissue site 116 may include providing the dressing 110, 410. The dressing 110, 410 may include the plurality of elongate fluid members 206 and the pneumatic connector 106. The elongate fluid members 206 may include the proximal end 212, the distal end 214, and the elongate side 216 between the proximal end 212 and the distal end 214. The pneumatic connector 106 may be positioned in fluid communication with the elongate fluid members 206. Further, the method may include positioning the elongate fluid members 206 across the tissue site 116, and positioning the pneumatic connector 106 through the external opening 117 of the tissue site 116. Further, the method may include moving a fluid from the tissue site 116 along the elongate fluid members 206 to the pneumatic connector 206, and extracting the fluid through the pneumatic connector 106.

Further, the method may include removing the elongate fluid members 206 from the tissue site 116 through the external opening 117 by applying a removal force to the pneumatic connector 106. In some embodiments, the removal force may be directed away from the tissue site 116. The removal force may include the pulling force 250. Further, in some embodiments, the method may include pulling the dressing 110, 410 from the tissue site 116 by the pneumatic connector 106.

In some embodiments, the tissue site 116 may be the abdominal cavity 124, and positioning the plurality of elongate fluid members 206 across the tissue site 116 may include placing at least one of the elongate fluid members 206 proximate to a paracolic gutter, such as the first paracolic gutter 128 or the second paracolic gutter 130, of the abdominal cavity 124. Further, in some embodiments, the method may include sealing the external opening 117 of the tissue site 116 at or about the pneumatic connector 106 of the dressing 110.

Referring to FIGS. 1-3, in some embodiments, removing elongate fluid members 206 from the tissue site 116 may include removing each of the elongate fluid members 206 through the external opening 117 one at a time. In some embodiments, removing the elongate fluid members 206 from the tissue site 116 may include separating the separable joint 210 between at least one of the elongate fluid members 206 and another of the elongate fluid members 206. In some embodiments, the separable joint 210 may be separated between at least one of the elongate fluid members 206 and another of the elongate fluid members 206 from exterior to the tissue site 116. In some embodiments, the separable joint 210 may be separated between at least one of elongate fluid members 206 and another of the elongate fluid members 206 from exterior to the tissue site 116 when the removal force is applied to the pneumatic connector 106.

Referring to FIGS. 1 and 4A-5B, in other embodiments, removing the plurality of elongate fluid members 206 from the tissue site 116 may include removing more than one of the elongate fluid members 206 through the external opening 117 at the same time. In other embodiments, positioning the elongate fluid members 206 across the tissue site 116 may include separating the separable joint 210 between at least one of the elongate fluid members 206 and another of the elongate fluid members 206, and spacing the elongate side 216 of at least one of the elongate fluid members 216 apart from the elongate side 216 of another of the elongate fluid members 206. In other embodiments, removing the elongate fluid members 206 from the tissue site 116 may include gathering the elongate side 216 of each of the elongate fluid members 206 together, and removing more than one the of elongate fluid members 206 through the external opening 117 at the same time. In other embodiments, gathering the elongate side 216 of each of the elongate fluid members 206 together may occur when the removal force is applied to the pneumatic connector 106 from exterior to the tissue site 116.

The systems, apparatuses, and methods described herein may provide significant advantages. Among other advantages, some embodiments may substantially reduce complications of trauma to the abdomen. For example, abdominal compartment syndrome (ACS) is a complication of trauma and some medical septic patients that has very high mortality and morbidity. Surgical decompression remains an important intervention. Decompression is achieved by opening the midline fascia along its full length. While this can result in improved physiologic response, the outcomes are not necessarily good. The open abdomen patient may be difficult to manage, susceptible to severe complications, and can require very long stays in an intensive care unit. The cost of treating these patients can be high, at least in part because of extremely long stays in a medical facility while the abdomen remains open. Further, additional complications can arise from ACS, such as kidney failure, which can result in very expensive adjunct therapies. Some of the embodiments described herein allow an abdomen to be closed with a dressing left in place to distribute negative pressure over a large manifolding area of the cavity, and the dressing can removed after treatment through a single exit point rather than the main incision of an open abdomen. The size and shape of some embodiments may also be customizable. Additionally or alternatively, some embodiments may also allow fluid drainage to be customized by location, and fluid removal may be maximized.

Although this specification discloses advantages in the context of certain illustrative, non-limiting embodiments, various changes, substitutions, permutations, and alterations may be made without departing from the scope of the appended claims. For example, a dressing such as the dressing 110 or the dressing 410 may be tapered toward an exit point to further facilitate removal. Further, any feature described in connection with any one embodiment may also be applicable to any other embodiment.

We claim:

1. A system for treating a tissue site, comprising:
   a fluid hub;
   a plurality of elongate fluid members positioned in fluid communication with the fluid hub, each of the plurality of elongate fluid members comprising a proximal end, a distal end, and an elongate side between the proximal end and the distal end, the elongate side extending outward from the fluid hub;
   a separable joint coupled between the elongate side of one of the plurality of elongate fluid members and the elongate side of another of the plurality of elongate fluid members, wherein the separable joint is carried by a portion of a dressing film defining the plurality of elongate fluid members, and wherein the dressing film is sealingly coupled around the separable joint;
   a pneumatic connector in fluid communication with the plurality of elongate fluid members; and
   a reduced-pressure source adapted to be positioned in fluid communication with the pneumatic connector.

2. The system of claim 1, wherein the fluid hub and the plurality of elongate fluid members are adapted to be positioned at the tissue site.

3. The system of claim 1, wherein the pneumatic connector is adapted to be positioned at an external opening of the tissue site.

4. The system of claim 1, wherein the pneumatic connector is adapted to extend through an external opening of the tissue site.

5. The system of claim 1, wherein the tissue site is an abdominal cavity, and wherein the plurality of elongate fluid members are adapted to be positioned at a paracolic gutter of the abdominal cavity.

6. The system of claim 1, wherein the proximal end or the distal end of the plurality of elongate fluid members is coupled to the fluid hub.

7. The system of claim 1, wherein the elongate side is positioned normal relative to the proximal end and the distal end of the plurality of elongate fluid members.

8. The system of claim 1, wherein each of the plurality of elongate fluid members are adapted to communicate fluid between the proximal end and the distal end.

9. The system of claim 1, wherein each of the plurality of elongate fluid members further comprise at least one fluid lumen positioned between the proximal end and the distal end.

10. The system of claim 9, wherein the at least one fluid lumen is positioned longitudinally in fluid communication between the proximal end and the distal end.

11. The system of claim 9, wherein the at least one fluid lumen extends substantially parallel to the elongate side.

12. The system of claim 9, wherein the at least one fluid lumen is defined by at least a portion of the dressing film, wherein the dressing film comprises a first dressing film and a second dressing film, and wherein the at least one fluid lumen is defined between the first dressing film and the second dressing film.

13. The system of claim 12, wherein the dressing film is comprised of a liquid impermeable material.

14. The system of claim 12, wherein the first dressing film is coupled to the second dressing film on opposing sides of the at least one fluid lumen.

15. The system of claim 12, further comprising a plurality of fenestrations disposed through at least one of the first dressing film and the second dressing film in fluid communication with the at least one fluid lumen.

16. The system of claim 12, wherein the at least one fluid lumen carries at least a portion of a dressing manifold.

17. The system of claim 16, wherein the dressing manifold is disposed in the at least one fluid lumen.

18. The system of claim 16, wherein the dressing film surrounds the dressing manifold.

19. The system of claim 16, wherein the dressing manifold comprises foam.

20. The system of claim 1, wherein the separable joint is configured to releasably couple the elongate side of one of the plurality of elongate fluid members to the elongate side of another of the plurality of elongate fluid members.

21. The system of claim 1, wherein the separable joint comprises perforations.

22. The system of claim 1, wherein the separable joint comprises a score.

23. The system of claim 12, wherein the separable joint is carried by a portion of the first dressing film and the second dressing film, and wherein the first dressing film is sealingly coupled to the second dressing film around the separable joint.

24. The system of claim 1, wherein the pneumatic connector comprises a tube.

25. The system of claim 1, wherein the pneumatic connector comprises a bridge manifold adapted to communicate fluid and surrounded by a bridge film, the bridge film comprising a liquid impermeable material.

26. The system of claim 1, wherein the pneumatic connector comprises a conduit interface.

27. The system of claim 1, wherein the pneumatic connector is coupled to at least one of the plurality of elongate fluid members and adapted to be accessible at an external opening of the tissue site to permit removal of the plurality of elongate fluid members from the tissue site.

28. The system of claim 1, wherein the plurality of elongate fluid members comprise a first elongate fluid member and a second elongate fluid member, the distal end of the first elongate fluid member coupled to the fluid hub and the proximal end of the second elongate fluid member coupled to the fluid hub, wherein the proximal end of the first elongate fluid member is in fluid communication with the distal end of the second elongate fluid member through the fluid hub.

29. The system of claim 28, wherein the pneumatic connector is coupled in fluid communication at the proximal end of the first elongate fluid member.

30. The system of claim 1, wherein the proximal end of each of the plurality of elongate fluid members are coupled to the fluid hub.

31. A dressing for treating a tissue site, comprising:
a fluid hub;
a first elongate fluid member including a first proximal end, a first distal end, and a first elongate side defined between the first proximal end and the first distal end, the first distal end coupled directly to the fluid hub
a second elongate fluid member including a second proximal end, a second distal end, and a second elongate side defined between the second proximal end and the second distal end, the second proximal end coupled to the fluid hub;
a separable joint coupled between the first elongate side and the second elongate side and configured to releasably couple the first elongate side to the second elongate side; and
a pneumatic connector coupled to the first proximal end of the first elongate fluid member, the pneumatic connector and the first proximal end of the first fluid member in fluid communication with the second distal end of the second fluid member through the fluid hub.

32. The dressing of claim 31, wherein the pneumatic connector is coupled to the first proximal end of the first elongate fluid member opposite from the fluid hub.

33. The dressing of claim 31, wherein the fluid hub comprises a first fluid hub and a second fluid hub, the first fluid hub coupled to the first distal end of the first elongate fluid member and the second proximal end of the second elongate fluid member, and the second fluid hub coupled to the second distal end of the second elongate fluid member.

* * * * *